US 9,877,855 B2

(12) United States Patent
Butler et al.

(10) Patent No.: US 9,877,855 B2
(45) Date of Patent: Jan. 30, 2018

(54) METHOD OF LOADING AND DELIVERING A SELF-EXPANDING STENT

(71) Applicant: Cook Medical Technologies LLC, Bloomington, IN (US)

(72) Inventors: James Butler, Aherlow (IE); Sean Cummins, Mungret (IE); Donagh O'Sullivan, Ballina-Killaloe (IE); Shane Holland, Monaleen (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 375 days.

(21) Appl. No.: 14/805,575

(22) Filed: Jul. 22, 2015

(65) Prior Publication Data

US 2016/0022456 A1    Jan. 28, 2016

Related U.S. Application Data

(60) Provisional application No. 62/029,174, filed on Jul. 25, 2014.

(51) Int. Cl.
*A61F 2/06*    (2013.01)
*A61F 2/962*    (2013.01)
*A61F 2/95*    (2013.01)

(52) U.S. Cl.
CPC ...... *A61F 2/962* (2013.01); *A61F 2002/9522* (2013.01)

(58) Field of Classification Search
CPC .......................... A61F 2/962; A61F 2002/9522
See application file for complete search history.

(56) References Cited

U.S. PATENT DOCUMENTS

| 4,580,568 | A | 4/1986 | Gianturco |
| 6,776,791 | B1 | 8/2004 | Stallings et al. |
| 7,942,924 | B1 | 5/2011 | Perez et al. |
| 8,261,420 | B2 * | 9/2012 | Von Oepen ............... A61F 2/91 29/235 |
| 9,492,274 | B2 * | 11/2016 | Johnson ................ A61F 2/2427 |
| 9,757,262 | B2 * | 9/2017 | Schreck .................. A61F 2/962 |
| 2004/0148007 | A1 * | 7/2004 | Jackson .................... A61F 2/95 623/1.12 |
| 2004/0199239 | A1 * | 10/2004 | Austin ...................... A61F 2/95 623/1.11 |
| 2005/0166389 | A1 * | 8/2005 | Perreault .................. A61F 2/95 29/508 |

(Continued)

OTHER PUBLICATIONS

Cardinal Search Report dated Feb. 20, 2014.

*Primary Examiner* — Eric Rosen
*Assistant Examiner* — Son Dang
(74) *Attorney, Agent, or Firm* — Brinks Gilson & Lione

(57) ABSTRACT

A method is provided for loading and delivering a self-expanding stent. The stent is compressed from its expanded diameter to a smaller delivery diameter. While compressed, the stent is pushed from the proximal end through the proximal end opening of a restraining sheath. The restraining sheath retains the stent in the delivery diameter. In order to deliver the stent, the proximal end of the stent is pushed and the restraining sheath is withdrawn proximally from the stent. As a result, the stent is released from the distal end opening of the restraining sheath.

20 Claims, 3 Drawing Sheets

(56) References Cited

U.S. PATENT DOCUMENTS

| | | | | |
|---|---|---|---|---|
| 2006/0142838 A1* | 6/2006 | Molaei | ............... | A61F 2/95 |
| | | | | 623/1.12 |
| 2007/0055358 A1* | 3/2007 | Krolik | ............... | A61F 2/91 |
| | | | | 623/1.31 |
| 2007/0079494 A1* | 4/2007 | Serrano | ............... | A61F 2/95 |
| | | | | 29/508 |
| 2007/0156223 A1* | 7/2007 | Vaughan | ............... | A61F 2/95 |
| | | | | 623/1.11 |
| 2007/0270932 A1* | 11/2007 | Headley | ............... | A61F 2/95 |
| | | | | 623/1.11 |
| 2009/0082840 A1* | 3/2009 | Rusk | ............... | A61F 2/95 |
| | | | | 623/1.11 |
| 2010/0049297 A1 | 2/2010 | Dorn | | |
| 2011/0015718 A1* | 1/2011 | Schreck | ............... | A61F 2/07 |
| | | | | 623/1.12 |
| 2012/0296407 A1 | 11/2012 | Caselnova | | |
| 2014/0018901 A1 | 1/2014 | Headley, Jr. et al. | | |
| 2014/0277357 A1* | 9/2014 | Slazas | ............... | A61F 2/966 |
| | | | | 623/1.12 |

* cited by examiner

METHOD OF LOADING AND DELIVERING A SELF-EXPANDING STENT

RELATED APPLICATIONS

This application claims the benefit of U.S. Provisional Patent Application No. 62/029,174, filed on Jul. 25, 2014, the entire contents of which are hereby incorporated by reference.

TECHNICAL FIELD

The present invention relates generally to medical devices and more particularly to methods of loading and delivering self-expanding stents.

BACKGROUND

Stents are used by physicians to treat numerous conditions using minimally invasive procedures. Stents may be characterized as either balloon-expandable or self-expanding. Balloon-expandable stents are made from a ductile material that plastically deforms as the stent is compressed and expanded. Thus, when a balloon-expandable stent is delivered into a body passageway, an outward force must be applied to the stent to plastically expand it against the tissues of the passageway. Typically, an inflatable balloon is used to apply the outward expansion force to the stent. By contrast, self-expanding stents are made from an elastic material. A self-expanding stent is typically designed with an expanded diameter that is slightly greater in size than the body passageway that the stent will be implanted within. In the expanded diameter, the elastic material of the stent is unstressed, or relaxed.

In order to deliver a self-expanding stent, the stent must be compressed from its expanded diameter to a smaller delivery diameter. While compressed into the delivery diameter, the stent is loaded into a restraining sheath that prevents the stent from expanding back to its expanded diameter. When a physician is ready to deliver the self-expanding stent into a patient's passageway, the physician introduces the restraining sheath and the compressed stent into the patient and locates the stent at the desired treatment site. The stent is then pushed axially out of the distal end opening of the restraining sheath within the patient's passageway. This releases the stent from the restraining sheath, and as a result, the stent elastically expands back toward its expanded diameter until it contacts the tissues of the passageway.

Delivery systems for self-expanding stents suffer from a number of problems that can interfere with reliable delivery of self-expanding stents. Because the stent is elastically compressed inside of the restraining sheath as it is pushed out of the sheath during delivery, friction occurs between the outer surface of the stent and the inner surface of the restraining sheath. Thus, sufficient axial force must be applied to the stent and the restraining sheath in order to overcome this frictional force in order to release the stent from the sheath. High frictional forces between the stent and the restraining sheath can lead to numerous undesirable consequences. In extreme situations, the physician may not be able to apply sufficient force to the stent and sheath to release the stent from the sheath. However, even where the physician is able to overcome the frictional forces to deliver the stent, the frictional force between the stent and the sheath may interfere with accurate positioning of the stent.

High frictional forces between a self-expanding stent and restraining sheath during delivery affect a number of components in the delivery system. In order to push the stent axially out of the restraining sheath, an inner catheter is typically provided that abuts the proximal end of the stent or otherwise contacts a portion of the stent. During release of the stent, the position of the inner catheter is typically retained in place and the restraining sheath is typically pulled proximally relative to the inner catheter. The inner catheter is designed to prevent the stent from moving proximally with the restraining sheath as it is pulled proximally. As a result, the stent remains axially in place while the restraining sheath slides proximally over and away from the stent.

During delivery, the restraining sheath is in tension due to the pulling force at the proximal end and the frictional force with the stent at the distal end. In opposition, the inner catheter is in compression due to the axial restraining force at the proximal end and the stent pushing back against the inner catheter at the distal end due to the friction. As a result, the restraining sheath can stretch during delivery, and if sufficient force is applied, the sheath may partially or completely tear or otherwise fail. The inner catheter may also compress in length, which causes the stent to move proximally as the inner catheter changes in length, at least until some point when the frictional force drops and the inner catheter springs back to its original length. The inner catheter may also buckle within the restraining sheath, which contributes to the change in length of the inner catheter. The inner catheter typically has a guidewire lumen extending axially therethrough, and the inner catheter may also plastically clamp down on the guidewire, which would then require the delivery system and the guidewire to be withdrawn together from the patient. The forces on the restraining sheath and inner catheter during delivery typically require the device manufacturer to design the components from relatively stiff materials to withstand the expected forces. However, this can lead to larger diameter delivery systems and can lead to kinking of the restraining sheath and inner catheter.

Accordingly, the inventors believe it would be desirable to minimize frictional forces between a self-expanding stent and the restraining sheath during delivery of the stent.

SUMMARY OF THE INVENTION

A method is described for loading a self-expanding stent into a restraining sheath and delivering the stent into a body passageway. The stent may be compressed in a stent crimper from an expanded diameter to a compressed diameter being smaller than the expanded diameter. The stent may have a series of struts interconnected by proximal bends and distal bends.

The restraining sheath retains the stent in the compressed diameter until the stent is released into the body passageway by withdrawing the restraining sheath proximally while a stop in the delivery system pushes on the proximal end of the stent. The stent may press outward against the inner surface of the restraining sheath. In order to load the stent into the restraining sheath, the stent is pushed into the proximal end opening of the restraining sheath. This causes the proximal bends in the stent structure to flare outward due to the pushing force required to push the stent into the sheath. The distal bends remaining unflared. Unlike conventional loading and delivery methods, the flared bends follow the unflared bends out the distal end opening of the restraining sheath which reduces friction between the outer surface of the stent and the inner surface of the sheath. The inventions herein may also include any other aspect described below in the written description, the claims, or in the attached drawings and any combination thereof.

BRIEF DESCRIPTION OF THE DRAWINGS

The invention may be more fully understood by reading the following description in conjunction with the drawings, in which.

DESCRIPTION OF THE PREFERRED EMBODIMENTS

Figure 1:
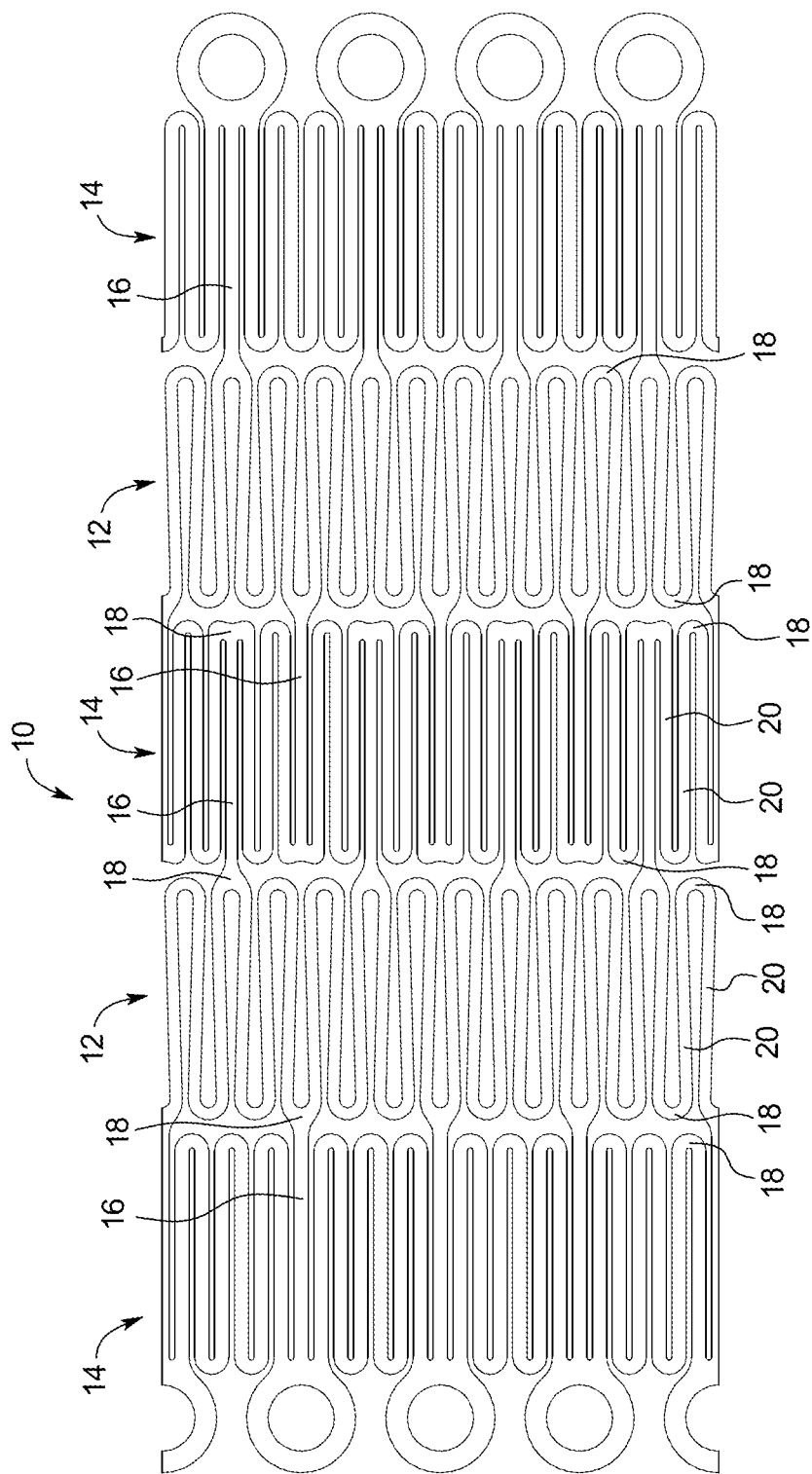
FIG. 1 is a plan view of a self-expanding stent in a compressed diameter.

Referring now to the figures, and particularly to FIG. 1, a self-expanding stent 10 is shown. The stent 10 is shown in FIG. 1 in a laid-out view for illustration purposes, but it is understood that the structure is tubular in shape with the top and bottom sides in FIG. 1 connected to each other. Although the stent structure 10 shown FIG. 1 is representative of a preferred stent structure 10, other stent structures may also be used. As shown, the stent 10 may be formed of a series of adjacent rings 12, 14 that are longitudinally connected to each other. Although each of the rings 12, 14 may be substantially equivalent to each other, the stent 10 may also be defined by different rings 12, 14 with distinct characteristics. For example, in the stent 10 of FIG. 1, the stent 10 is defined by flex rings 12 and hoop rings 14. In the flex rings 12, the ring 12 winds around the stent 10 in a sinusoidal pattern, and the longitudinal connectors 16 do not pass through the ring 12. That is, the longitudinal connectors 16 connect to the outside of the ring 12 at a bend 18. In contrast, the hoop rings 14 wind around in a similar sinusoidal pattern, but the longitudinal connectors 16 pass longitudinally through the ring 14. That is, the longitudinal connectors 16 that connect to the proximally adjacent ring 12 extend distally through the hoop ring 14, and the longitudinal connectors 16 that connect to the distally adjacent ring 12 extend proximally through the hoop ring 14. As a result, the flex rings 12 are axially more flexible; while the hoop rings 14 are stiffer and provide a greater radial outward expansion force. The combination of flex rings and hoop rings 12, 14 provides a desirable combination of axial flexibility and outward radial force.

Figure 2:
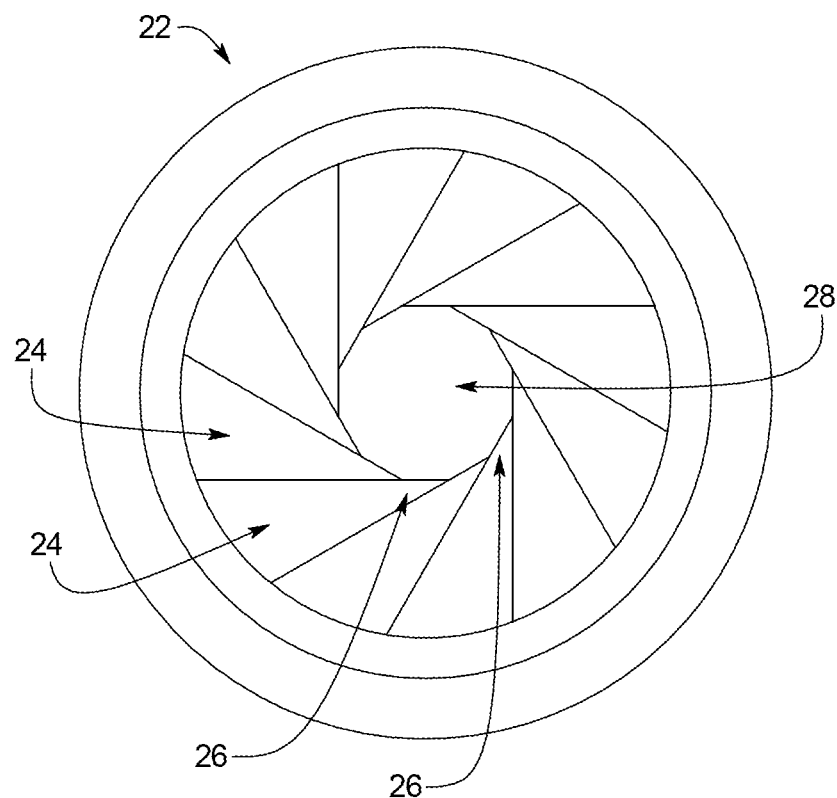
FIG. 2 is an end view of a stent crimper.

The stent 10 in FIG. 1 is shown in the compressed delivery diameter. It is understood that when the stent 10 is released, the elastic expansion of the stent 10 causes the bends 18 in the rings 12, 14 to widen and adjacent struts 20 to spread apart from each other until the stent 10 reaches its relaxed, unstressed state. In order to compress the stent 10 for loading, an expanded stent 10 may be placed into a stent crimper 22 like the crimper 22 shown in FIG. 2. The crimper 22 shown in FIG. 2 has a series of triangular-shaped dies 24 that are circumferentially adjacent to each other. The tips 26 of the dies 24 define an axial passageway 28 through the crimper 22. The size of the passageway 28 can be enlarged and reduced by actuating the dies 24. Thus, in use, the dies 24 are actuated to enlarge the passageway 28 so that the passageway 28 is larger than the expanded diameter of the stent 10. The stent 10 is then axially inserted into the passageway 28. The dies 24 are then actuated to reduce the size of the passageway 28. This causes the tips 26 of the dies 24 to press inward on the outer surface of the stent 10 to compress the stent 10. Once the stent 10 reaches the desired compressed diameter, movement of the dies 24 is stopped and the dies 24 are retained in place to keep the stent 10 in the compressed diameter. However, it is understood that other types of stent crimpers may also be used.

Figure 3:
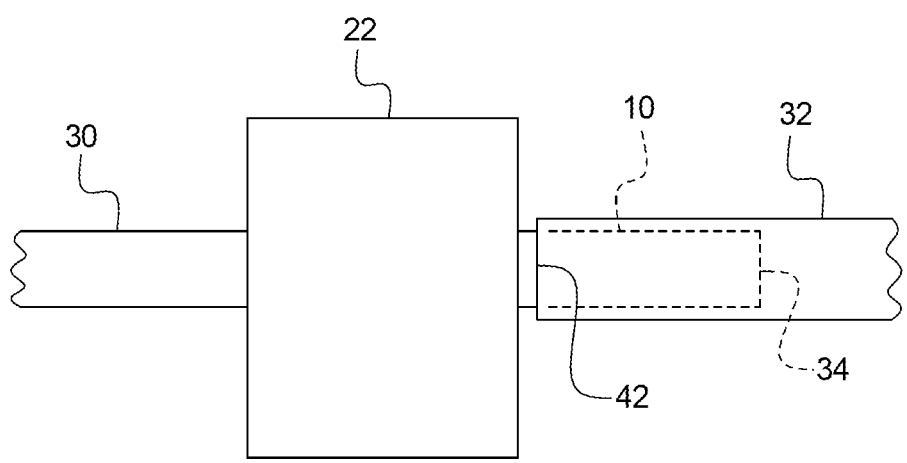
FIG. 3 is a side schematic view of a stent being loaded from the stent crimper into a restraining sheath.

As shown in FIG. 3, the stent 10 is then pushed out of the stent crimper 22 while it is in its compressed diameter. Typically, the stent 10 is pushed out of the crimper 22 with a quill 30 that has a diameter substantially equal to the diameter of the compressed stent. Thus, the quill 30 may be pushed through the passageway 28 of the crimper 22 from one side of the crimper 22 to push the stent 10 out the other side of the crimper 22. The restraining sheath 32 may be positioned adjacent the side of the crimper 22 that the stent 10 is pushed out of so that the stent 10 is pushed directly into the sheath 32 in the compressed diameter. Alternatively, the stent 10 could be pushed from the crimper 22 into a temporary tube, and then pushed from the tube into the restraining sheath 32 in a similar manner described above.

Figure 4:
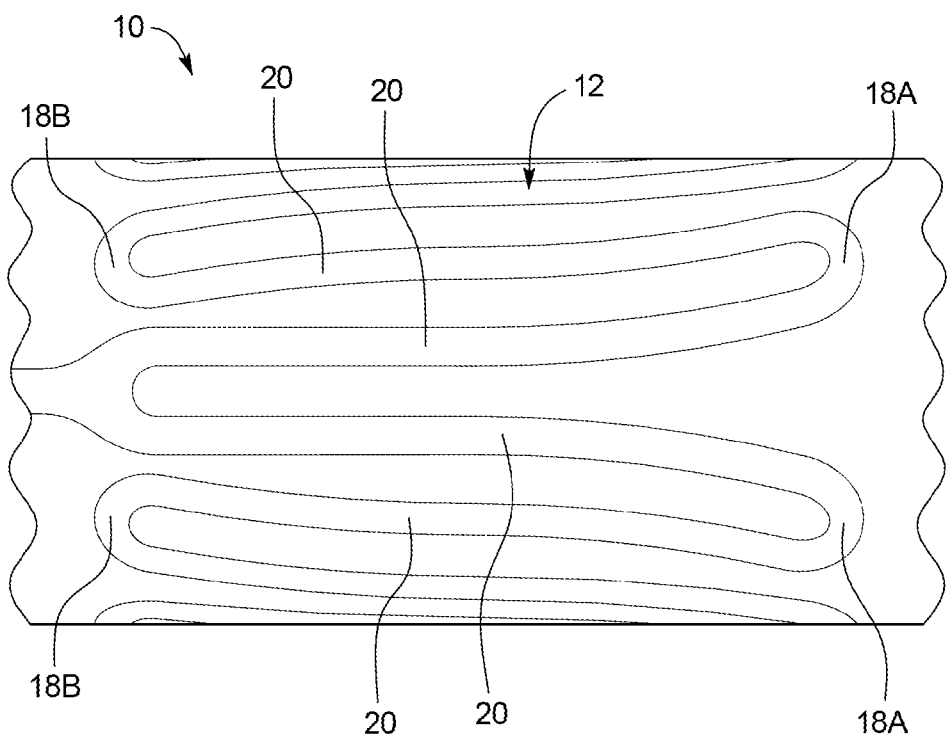
FIG. 4 is an enlarged view of a portion of the stent showing flared and unflared bends.

One problem that the inventors have discovered is illustrated in FIG. 4. FIG. 4 is an enlarged view of a flex ring 12 in the compressed diameter after it has been loaded into a restraining sheath 32. As illustrated, the bends 18A on the right side of the ring 12 are flared 18A outward, and the bends 18B on the left side are unflared 18B. The unflared bends 18B may also be tapered inward slightly. The outward flaring of the bends 18A occurs during the loading process due to the pushing force that is required to push the compressed stent 10 into the restraining sheath 32. Thus, the flaring occurs on the bends 18A that are on the side of the ring 12 that is closest to the end that is pushed on with the quill 30. While flaring has been identified as a potential problem in the flex rings 12, it is also possible that the hoop rings 14 or other types of stent structures could suffer from flaring in certain circumstances. Flaring as illustrated in FIG. 4 may be a more significant problem for stents 10 that experience higher frictional forces during loading. For example, flaring may be less of a concern when relatively short stents 10 are used due to the lower overall friction that results because of the shorter length of conventional stents 10. However, longer stents 10, such as 100 millimeters (mm) and longer stents 10, and particularly 120 mm and longer stents 10, are more likely to suffer from flaring problems due to the higher total friction that occurs during loading. It is also possible that stents 10 with rough or stickier outer surfaces that increase friction with the restraining sheath 32 may cause flaring problems. For example, stents 10 that are coated with a drug coating on the surfaces of the stent structure 10, as opposed to uncoated, bare stents 10, may result in higher friction and more flaring. Flaring is particularly likely when drug coatings are used on stents 10 that are 100 mm or 120 mm and longer.

In conventional delivery systems and methods of loading, the distal end 34 of the stent 10 is pushed by the quill 30 so that the proximal end 36 of the stent 10 slides first through the distal end opening 38 of the restraining sheath 32. This conventional loading process is typically preferred because in the loaded delivery system 40, the distal end 34 of the stent 10 will be positioned adjacent the distal end opening 38 of the restraining sheath 32 such that the entire outer surface of the stent 10 is in contact with the inner surface of the restraining sheath 32. Thus, pushing the stent 10 through the distal end opening 38 of the restraining sheath 32 results in the least amount of stent travel possible. Also, it is relatively easy to position the distal end 34 of the stent 10 adjacent the distal end opening 38 of the sheath 32 by monitoring the distal end 34 of the stent 10 and the end of the quill 30 in contact therewith during the loading process.

The inventors, however, have discovered that conventional loading processes can result in the distal bends of the stent rings 12, 14 being flared 18A within the restraining sheath 32. That is, in a conventional loading process, the flared bends 18A on the right side of FIG. 4 would be located closer to the distal end opening 38 of the restraining sheath 32 than the unflared bends 18B on the left side of FIG. 4. Thus, when the restraining sheath 32 is withdrawn proximally during delivery of the stent 10, the flared bends 18A lead ahead of the unflared bends 18B as the stent 10 slides along the inner surface of the sheath 32. As a result, the flared bends 18A can potentially dig into the inner surface of the sheath 32 and cause scraping and increased friction therebetween. This may be a particular problem where the inner surface of the restraining sheath 32 is made from a polymer that permits the flared bends 18A to dig into the sheath 32 surface, like polytetrafluoroethylene (PTFE). Stents without a graft layer surrounding the stent structure 10 may also be more susceptible to this problem because a graft layer may have a tendency to resist flaring of stent bends 18A and may also tend to isolate any flared bends 18A from the inner surface of the restraining sheath 32 during delivery. With the flared bends 18A sliding first along the sheath 32, higher delivery forces may be required to withdraw the stent 10, and in extreme situations, the stent 10 could be prevented from being released from the sheath 32. Higher delivery forces also require more robust delivery systems 40 and design sacrifices as noted above.

By contrast, in one improved loading and delivery method, the proximal end 36 of the stent 10 is pushed so that the distal end 34 of the stent 10 is pushed through and slides first through the proximal end opening 42 of the restraining sheath 32. In order to position the distal end 38 of the stent 10 adjacent the distal end opening 38 of the restraining sheath 32, the stent 10 is pushed along the entire length of the restraining sheath 32 unlike conventional loading methods. Because the proximal end 36 of the stent 10 is pushed during loading, as opposed to the distal end 34, the unflared bends 18B on the left side of FIG. 4 will be located closer to the distal end opening 38 of the restraining sheath 32 than the flared bends 18A on the right side of FIG. 4. Thus, when the restraining sheath 32 is withdrawn during delivery of the stent 10. The flared bends 18A follow the unflared bends 18B. Thus, in the improved method, unflared bends 18B lead ahead of the flared bends 18A as the stent 10 slides along the inner surface of the sheath 32. Because the flared bends 18A follow instead of lead during delivery of the stent 10, the flared bends 18A slide smoothly along the inner surface of the sheath 32 without substantially digging into the sheath 32. This reduces the forces needed to deliver the stent 10 and minimizes damage to the delivery system 40 and/or stent 10 during delivery.

Figure 5:
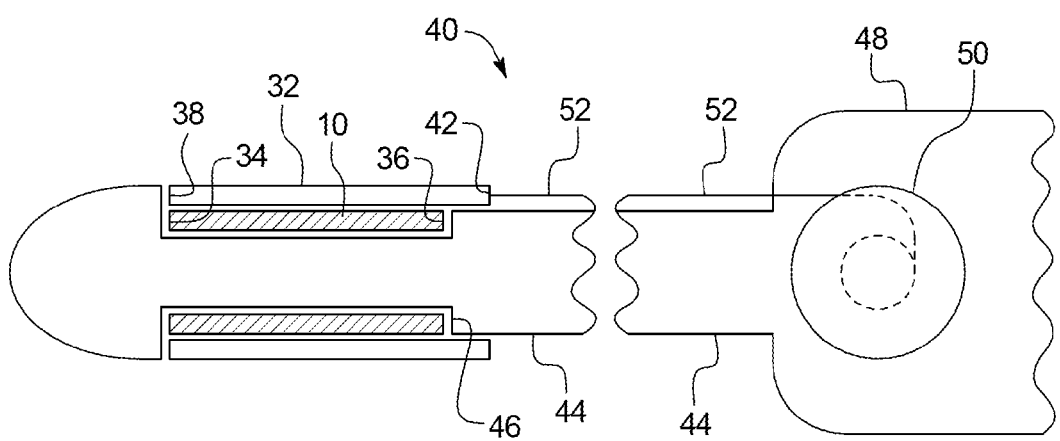
FIG. 5 is a cross-sectional schematic view of a delivery system for the stent.

As shown in FIG. 5, the restraining sheath 32 is attached to a delivery system 40 for delivering a stent 10 into a body passageway. The delivery system 40 may have an inner catheter 44 with a stop 46 located adjacent the proximal end 36 of the stent 10. The inner catheter 44 extends proximally to a handle 48 and is typically attached to the handle 48 so that the physician can maintain the inner catheter 44, and stent 10, in the desired longitudinal position by holding the handle 48 in a fixed position. The handle 48 is also designed to withdraw the restraining sheath 32 relative to the inner catheter 44 and the stent 10. The restraining sheath 32 may be withdrawn by the handle 48 in a number of ways, but in FIG. 5, the handle 48 is provided with a spool 50. A wire 52 is connected to the spool 50 and extends distally from the handle 48 to the restraining sheath 32 where the wire 52 is connected to the sheath 32. Thus, the restraining sheath 32 may be withdrawn by rotating the spool 50 to wind up the wire 52 on the spool 50. When the distal end 34 of the stent 10 is pushed through the proximal end 42 of the restraining sheath 32 as illustrated in FIG. 3, it is preferable to use, a shorter length sheath 32 since the stent 10 is pushed along the full length of the sheath 32 during loading. Thus, it is preferred for the proximal end 42 of the restraining sheath 32 to be located distal from the handle 48 in the assembled delivery system 40 and for the sheath 32 to be connected to the handle 48 with a wire 52 or other component. In particular, it is preferred for the length of the restraining sheath 32 between its proximal and distal ends 42, 38 to be less than two times the length of the stent 10. It may also be preferable for the length of the restraining sheath 32 to be no more than 50 mm longer than the length of the stent 10. By keeping the length of the restraining sheath 32 relatively short, the distance that the stent 10 is pushed during loading can be reduced and flaring of the proximal bends 18A can be minimized.

Alternatively, the restraining sheath 32 may be a full length restraining sheath 32 extending all the way to the handle 48 where the sheath 32 is attached to the handle 48. Thus, the restraining sheath 32 may be pulled directly at the handle 48 to withdraw the restraining sheath 32 without the need for a wire 52. While the distal end 34 of the stent 10 could be pushed through the proximal end 42 of a full length restraining sheath 32 until the distal end 34 of the stent 10 is adjacent the distal end 38 of the restraining sheath 32, this approach would typically have the disadvantage of having to push the stent 10 a significant distance through the restraining sheath 32 before reaching the distal end 38 of the restraining sheath 32. Another approach that may be used with a full length restraining sheath 32 as well as a shorter length sheath 32 if desired is to push the stent 10 into a temporary tube from the crimper 22. If the outer diameter of the temporary tube is less than the inner diameter of the restraining sheath 32, the temporary tube may be inserted through the restraining sheath 32 at least partially or until the distal end 34 of the stent 10 is adjacent the distal end 38 of the restraining sheath 32. The temporary tube may then be withdrawn from the stent 10 while pushing on the proximal end 36 of the stent 10 by sliding the tube proximally or by rolling and/or pealing the tube proximally. The stent 10 will then expand within the restraining sheath 32 until the entire outer surface of the stent 10 contacts the inner surface of the restraining sheath 32. However, a possible disadvantage of this approach is that the stent 10 needs to be compressed to a smaller diameter to fit into the temporary tube than the final diameter that the stent 10 will be compressed to within the restraining sheath 32.

While preferred embodiments of the inventions have been described, it should be understood that the inventions are not so limited, and modifications may be made without departing from the inventions herein. While each embodiment described herein may refer only to certain features and may not specifically refer to every feature described with respect to other embodiments, it should be recognized that the features described herein are interchangeable unless described otherwise, even where no reference is made to a specific feature. It should also be understood that the advantages described above are not necessarily the only advantages of the inventions, and it is not necessarily expected that all of the described advantages will be achieved with every embodiment of the inventions. The scope of the inventions is defined by the appended claims, and all devices and methods that come within the meaning of the claims, either literally or by equivalence, are intended to be embraced therein.

The invention claimed is:

1. A method for loading and delivering a self-expanding stent, comprising:
   compressing said stent in a stent crimper from an expanded diameter to a compressed diameter being smaller than the expanded diameter, said stent comprising a series of struts interconnected by proximal bends and distal bends;
   loading said stent into a restraining sheath by pushing on a proximal end of said stent when said stent is in said compressed diameter, said proximal bends being flared outward against an inner surface of said restraining sheath in response to said pushing and said distal bends remaining unflared, said proximal end of said stent being pushed until an entire outer surface of said stent contacts the inner surface of said restraining sheath and a distal end of said stent is proximate a distal end of said restraining sheath;
   attaching said restraining sheath being loaded with said stent to a delivery system, said delivery system comprising a stop disposed adjacent said proximal end of said stent and a handle adapted to withdraw said restraining sheath proximally relative to said stop; and
   delivering said stent by manipulating said handle to withdraw said restraining sheath, said stop pushing on said proximal end of said stent to restrain said stent longitudinally while said restraining sheath is withdrawn proximally from said stent, said stent pressing outward against said inner surface of said restraining sheath as said restraining sheath slides proximally along an exterior surface of said stent, wherein said unflared distal bends slide against said inner surface of said restraining sheath respectively ahead of said flared proximal bends.

2. The method according to claim 1, wherein the step of loading said stent comprises loading said stent wherein said inner surface of said restraining sheath comprises polytetrafluoroethylene.

3. The method according to claim 1, wherein the step of compressing said stent comprises compressing said stent being at least 100 mm long.

4. The method according to claim 3, wherein the step of compressing said stent comprises compressing said stent being at least 120 mm long.

5. The method according to claim 1, wherein the step of loading said stent comprises loading said stent wherein said distal end of said stent is pushed through a proximal end of said restraining sheath.

6. The method according to claim 1, wherein the step of attaching said restraining sheath comprises attaching said restraining sheath wherein a proximal end of said restraining sheath is disposed distal from said handle.

7. The method according to claim 6, wherein the step of attaching said restraining sheath comprises attaching said restraining sheath being connected to said handle with a wire, said wire being pulled to withdraw said restraining sheath.

8. The method according to claim 1, wherein the step of loading said stent comprises loading said stent wherein a length of said restraining sheath between a proximal end of said restraining sheath and said distal end of said restraining sheath is less than two times a length of said stent between said proximal end of said stent and said distal end of said stent.

9. The method according to claim 1, wherein the step of loading said stent comprises loading said stent wherein a length of said restraining sheath between said proximal end of said restraining sheath and said distal end of said restraining sheath is no more than 50 mm longer than a length of said stent between said proximal end of said stent and said distal end of said stent.

10. The method according to claim 1, wherein the step of attaching said restraining sheath comprises attaching said restraining sheath wherein a proximal end of said restraining sheath extends to and is attached to said handle.

11. The method according to claim 1, wherein the step of loading said stent comprises loading said stent into said restraining sheath directly from said stent crimper.

12. The method according to claim 1, wherein the step of loading said stent comprises loading said stent being at least 100 mm long, said distal end of said stent is pushed through a proximal end of said restraining sheath, and said proximal end of said restraining sheath is disposed distal from said handle.

13. The method according to claim 12, wherein the step of loading said stent comprises loading said stent wherein a length of said restraining sheath between said proximal end of said restraining sheath and said distal end of said restraining sheath is less than two times a length of said stent between said proximal end of said stent and said distal end of said stent.

14. The method according to claim 13, wherein the step of attaching said restraining sheath comprises attaching said restraining sheath being connected to said handle with a wire, said wire being pulled to withdraw said restraining sheath.

15. The method according to claim 14, wherein the step of loading said stent comprises loading said stent into said restraining sheath directly from said stent crimper.

16. The method according to claim 15, wherein the step of compressing said stent comprises compressing said stent being at least 120 mm long.

17. The method according to claim 16, wherein the step of loading said stent comprises loading said stent wherein a length of said restraining sheath between said proximal end of said restraining sheath and said distal end of said restraining sheath is no more than 50 mm longer than a length of said stent between said proximal end of said stent and said distal end of said stent.

18. The method according to claim 17, wherein the step of loading said stent comprises loading said stent wherein said inner surface of said restraining sheath comprises polytetrafluoroethylene.

19. The method according to claim 1, wherein the step of loading said stent comprises loading said stent wherein said inner surface of said restraining sheath comprises polytetrafluoroethylene, and said stent is at least 120 mm long.

20. The method according to claim 19, wherein the step of loading said stent comprises loading said stent wherein said distal end of said stent being pushed through a proximal end of said restraining sheath, and said proximal end of said restraining sheath is disposed distal from said handle, and a length of said restraining sheath between said proximal end of said restraining sheath and said distal end of said restraining sheath is less than two times a length of said stent between said proximal end of said stent and said distal end of said stent.

* * * * *